United States Patent
Feiring et al.

(10) Patent No.: US 10,029,248 B2
(45) Date of Patent: Jul. 24, 2018

(54) MEMBRANE SEPARATION OF OLEFIN AND PARAFFIN MIXTURES

(71) Applicant: COMPACT MEMBRANE SYSTEMS INC., Newport, DE (US)

(72) Inventors: Andrew Edward Feiring, Wilmington, DE (US); Jonathan Lazzeri, Ventura, CA (US); Sudipto Majumdar, Newark, DE (US); Ning Shangguan, Cherry Hill, NJ (US)

(73) Assignee: COMPACT MEMBRANE SYSTEMS INC., Newport, DE (US)

( * ) Notice: Subject to any disclaimer, the term of this patent is extended or adjusted under 35 U.S.C. 154(b) by 426 days.

(21) Appl. No.: 14/334,605

(22) Filed: Jul. 17, 2014

(65) Prior Publication Data

US 2015/0025293 A1 Jan. 22, 2015

Related U.S. Application Data

(60) Provisional application No. 61/847,899, filed on Jul. 18, 2013.

(51) Int. Cl.
| | |
|---|---|
| *B01J 47/12* | (2017.01) |
| *B01J 41/14* | (2006.01) |
| *B01J 39/20* | (2006.01) |
| *C07C 7/144* | (2006.01) |
| *B01D 53/22* | (2006.01) |
| *B01D 71/76* | (2006.01) |
| *B01D 71/82* | (2006.01) |
| *B01D 71/32* | (2006.01) |
| *B01D 71/52* | (2006.01) |

(52) U.S. Cl.
CPC ............ *B01J 47/12* (2013.01); *B01D 53/228* (2013.01); *B01D 71/76* (2013.01); *B01D 71/82* (2013.01); *B01J 39/20* (2013.01); *B01J 41/14* (2013.01); *C07C 7/144* (2013.01); *B01D 71/32* (2013.01); *B01D 71/52* (2013.01); *Y02P 20/51* (2015.11)

(58) Field of Classification Search
USPC ...................................................... 521/27, 31
See application file for complete search history.

(56) References Cited

U.S. PATENT DOCUMENTS

| | | | |
|---|---|---|---|
| 3,758,603 A | 9/1973 | Steigelmann et al. | |
| 3,758,605 A | 9/1973 | Hughes et al. | |
| 4,614,524 A | 9/1986 | Kraus | |
| 4,731,263 A | 3/1988 | Martin et al. | |
| 5,015,268 A | 5/1991 | Ho | |
| 5,062,866 A | 11/1991 | Ho | |
| 5,191,151 A * | 3/1993 | Eriksen | B01D 67/0093 585/818 |
| 5,670,561 A | 9/1997 | Pinnau et al. | |
| 6,468,331 B2 | 10/2002 | Kang et al. | |
| 6,706,771 B2 | 3/2004 | Kim et al. | |
| 6,878,409 B2 | 4/2005 | Kim et al. | |
| 7,179,321 B2 | 2/2007 | Kang et al. | |
| 7,220,508 B2 * | 5/2007 | Watakabe | B01D 71/44 429/494 |
| 7,361,800 B2 | 4/2008 | Hererra et al. | |
| 7,491,262 B2 | 2/2009 | Kang et al. | |
| 2007/0088142 A1 | 4/2007 | Ikeda et al. | |
| 2016/0164129 A1* | 6/2016 | Amemiya | H01M 8/1004 429/481 |

* cited by examiner

*Primary Examiner* — Mark Kaucher
*Assistant Examiner* — Henry Hu
(74) *Attorney, Agent, or Firm* — Devlin Law Firm LLC; James M. Lennon

(57) ABSTRACT

A metal exchanged fluorinated ionomer is a copolymer minimally including repeating units of (i) a polymerized derivative of a perfluorinated cyclic or cyclizable monomer and (ii) a strong acid highly fluorinated vinylether compound in which the acid moiety is exchanged with a cation of a Group 11 metal. Metal exchanged fluorinated ionomers are readily soluble and can be formed into thin, selectively gas permeable membranes by solution deposition methods. These membranes are suitable for separating olefins from gas olefin/paraffin mixtures. Good selectivity and transmembrane flux can be obtained without humidifying the membrane feed gas mixture.

19 Claims, No Drawings

MEMBRANE SEPARATION OF OLEFIN AND PARAFFIN MIXTURES

GOVERNMENT RIGHTS

Support was provided under Department of Energy awards of DE-SC0004672 and DE-SC0007510. The U.S. government has rights in this patent application.

FIELD OF THE INVENTION

This invention relates to the membrane separation mainly of olefin hydrocarbons from olefin/paraffin hydrocarbon mixtures. More particularly, the present invention relates to a type of a fluorinated polymeric membrane suitable for the facilitated transport separation of olefins from mixtures of olefins and paraffins in which a facilitating moiety is on the backbone of the polymeric membrane.

BACKGROUND OF THE INVENTION

Olefin compounds, such as ethylene and propylene, are important raw materials in the current petrochemical industry. They are largely obtained from crude petroleum by high temperature thermal decomposition and purification processes. Paraffin compounds, such as ethane and propane are also produced by the thermal decomposition steps. As a result, olefin production usually produces a mixture of olefins and paraffins. A separation process of mixtures of olefins and paraffins is very frequently needed to obtain olefin purity suitable as raw material in subsequent end use processing. The separation of ethylene from mixtures with ethane is an exemplary process of extreme industrial importance that continues to this day.

Traditionally, fractional distillation has been used for such separations and the associated unit operations have many drawbacks, such as high energy consumption, large equipment costs, labor costs, safety concerns and the like. For example, to separate ethylene/ethane mixture, a typical distillation process reportedly can involve using a distillation column incorporating contact area equivalent to least 100 theoretical trays operating at a high pressure of about 23 atm and sub-zero degree temperature. In the separation of propylene/propane, similar operation conditions at higher temperatures are also required.

Membrane technology has been considered to replace distillation for olefin-paraffin separation. Commercially practical separation of many important olefin/paraffin mixtures, for example ethylene/ethane, has been difficult to accomplish using selectively permeable polymeric membranes. Traditional polymeric membranes cannot discriminate well between ethylene and ethane with commercially attractive productivity because these compounds are similar in both molecular size and physical properties that affect selective permeability.

Facilitated transport membrane separation ("FTMS") has arisen as an effective type of membrane process to separate olefins from paraffins. Mass transfer via FTMS is accomplished by traditional solution diffusion coupled with a selectivity-enhancing carrier mechanism. In early-developed, liquid state forms of FTMS, the carrier is in a liquid on the surface or in the pores of a membrane serving to maintain the liquid carrier adjacent to the feed side or immobilized within the membrane. To transfer across the membrane, a component of the feed associates with the carrier to become a part of the liquid carrier phase. The component and carrier travel through the membrane as a unit under an appropriate driving force. They separate on the far side discharging desired feed component(s) into the permeate stream for an end use purpose.

For separations of olefin/paraffin mixtures, a typical liquid carrier is an aqueous solution containing a metal salt. Olefin components associate preferentially with the carrier by reversibly complexing with the metal of the salt. A complexed olefin can transfer across the liquid filled membrane with significantly higher selectivity relative to the undesired paraffin feed components, than can be achieved by the non-metal-complexed olefin.

Liquid state FTMS functions for olefin/paraffin separations to an extent but has drawbacks. A principal flaw is gradual depletion of carrier that causes permeance to diminish with service time. Also, solvent or other moieties present in the liquid carrier that escape into the permeate stream need to be removed from the desired product components.

Among various techniques that have been reported to improve upon functionality of liquid state FTMS is a solid state membrane process. Some developments in this area are summarized as follows.

In U.S. Pat. No. 5,015,268 to Ho a solid homogeneous FTMS membrane is prepared from a hydrophilic polymer such as polyvinyl alcohol. The membrane does not have a liquid carrier. A metal ion or metal salt capable of complexing with aliphatically unsaturated hydrocarbons, for example silver nitrate, is distributed homogeneously in the hydrophilic polymer. Preferably the polymer is crosslinked.

Kimura et al. in U.S. Pat. No. 4,318,714 discloses FTMS using a polymeric ion exchange membrane in which the polymer has electrostatically retained counter ions reversibly reactive to the gas molecules being separated. Example 4 describes high selectivity by pure component separation of ethylene and ethane by sulfonated polyxylylene oxide ion exchange resin that was immersed in $AgNO_3$ solution then rinsed in distilled water to remove residual $AgNO_3$ solution and $Ag^+$ ions. The feed gases were humidified to 90% relative humidity.

U.S. Pat. No. 4,614,524 to Kraus used a membrane of halogenated olefin polymer with pendant acid groups (i.e., Nafion® 415 ion exchange resin) that was equilibrated with $AgNO_3$ to obtain selectivity between ethylene and ethane. Kraus teaches that the membrane must be plasticized with a polyhydric alcohol to effect separation.

Eriksen et al. U.S. Pat. No. 5,191,151 discloses a process for separating $C_2$-$C_4$ olefins from $C_1$-$C_6$ paraffins using a membrane of an ion exchange resin of tetrafluoroethylene/perfluorovinylether sulfonated copolymer with $Ag^+$ ion exchange. The membrane is prepared by certain specific ion exchange methods that includes steps of converting the poly(perfluorosulfonic acid) from protonic form to anionic —$SO_3^-$ form by contacting with an alkali metal solution, swelling the converted membrane in an alcohol, and exchanging a silver ion in the ionomer. For the membrane to separate olefin from paraffin, the gas mixture feed must be humidified.

The development of a facilitated transport separation membrane that provides high selectivity and permeance in separating olefins from gas mixtures with paraffins is greatly desired. It is further desired to have such a membrane that functions in olefin/paraffin separation with little or no limitation of humidification of the feed or plasticization of the membrane. There is much need for an olefin/paraffin membrane separation process that maintains high selectivity and permeance for extended durations. A method of manufacturing consistently high quality facilitated transport separation membranes effective to separate olefins from mixtures with paraffins with both high selectivity and permeance is also much wanted.

SUMMARY OF THE INVENTION

The novel metal exchanged fluorinated ionomer is a copolymer minimally including two repeating unit types. These are the polymerized derivative of a perfluorinated cyclic or cyclizable monomer and a strong acid highly fluorinated vinylether compound in which the acid moiety is exchanged with a cation of a Group 11 metals. Selected metal exchanged fluorinated ionomers are readily soluble and can be formed into thin, selectively gas permeable membranes by solution deposition methods. These membranes are suitable for separating olefins from olefin/paraffin mixtures. Good selectivity and transmembrane flux properties can be obtained without humidifying the membrane feed gas mixture.

Accordingly there is provided a solid state separation membrane comprising a nonporous selectively permeable layer consisting essentially of a metal exchanged fluorinated ionomer comprising repeating units A and B in which A is a polymerized derivative of a perfluorinated cyclic or cyclizable organic compound, and B has the formula

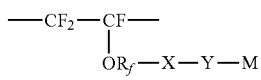

in which X is $SO_2$ or CO, Y is $NSO_2R_f^1$ or O, $R_f$ and $R_f^1$ are each independently perfluoroalkyl or perfluoroalkylether groups having 1-20 carbon atoms, and M is a Group 11 metal, and in which the ion exchanged fluorinated ionomer comprises m and n fractions of total number of repeating units A and B respectively, each of m and n being greater than 0 and less than 1.0.

There is also provided a method of making a metal exchanged fluorinated ionomer for use in membrane separation of olefins from paraffins, comprising the steps of: (A) providing a hydrolyzed copolymer comprising repeating units A being a polymerized derivative of a perfluorinated cyclic or cyclizable organic compound and repeating units B having the formula

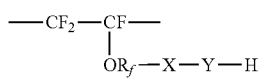

in which X is $SO_2$ or CO, Y is $NSO_2R_f^1$ or O, and $R_f$ and $R_f^1$ are each independently perfluoroalkyl or perfluoroalkylether groups having 1-20 carbon atoms, (B) dissolving the hydrolyzed copolymer in a liquid comprising a polar solvent to form a polymer solution, (C) providing a stoichiometric excess of fine particles of a metal salt of a Group 11 metal, (D) charging the fine particles of the metal salt to the polymer solution and agitating the polymer solution with intensity effective to maintain the particles in a uniform dispersion in the polymer solution for a duration effective to exchange the Group 11 metal with the acid form copolymer thereby forming a metal exchanged fluorinated ionomer, (E) filtering the dispersion to remove substantially all residual particles of the metal salt and thereby providing a metal exchanged fluorinated ionomer solution.

There is further provided a method of making a membrane for the separation of olefins from a mixture with paraffins, comprising the steps of: (I) providing a metal exchanged fluorinated ionomer solution produced by a method comprising the following steps (A) providing metal exchanged fluorinated ionomer comprising repeating units A and B in which A is a polymerized derivative of a perfluorinated cyclic or cyclizable organic compound, B has the formula

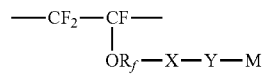

in which X is $SO_2$ or CO, Y is $NSO_2R_f^1$ or O, $R_f$ and $R_f^1$ are each independently perfluoroalkyl or perfluoroalkylether groups having 1-20 carbon atoms, and M is a Group 11 metal, (B) dissolving the metal exchanged fluorinated ionomer in a liquid comprising a polar solvent to form a metal exchanged fluorinated ionomer solution, (II) coating a substrate with the metal exchanged fluorinated ionomer solution, and (III) evaporating the liquid from the metal exchanged fluorinated ionomer solution, thereby forming membrane comprising a dry, solid state, nonporous layer of metal exchanged fluorinated ionomer.

Also provided is a method of separating an olefin from a feed mixture of the olefin with a paraffin comprising the following steps: (A) providing a selectively permeable membrane comprising a nonporous active layer consisting essentially of a metal exchanged fluorinated ionomer comprising repeating units A and B in which A is a polymerized derivative of a perfluorinated cyclic or cyclizable organic compound, B has the formula

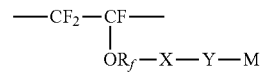

in which X is $SO_2$ or CO, Y is $NSO_2R_f^1$ or O, $R_f$ and $R_f^1$ are each independently perfluoroalkyl or perfluoroalkylether groups having 1-20 carbon atoms, and M is a Group 11 metal, (B) contacting a feed side of the selectively permeable membrane with the feed mixture, (C) applying a driving force for permeation of the feed mixture through the selectively permeable membrane, thereby causing the olefin to selectively permeate to a permeate side of the membrane, and (D) collecting an olefin-enriched permeate product.

Yet further this invention provides a metal exchanged ionomer solution comprising (I) a liquid solvent system comprising a polar solvent, and (II) a metal exchanged fluorinated ionomer comprising repeating units A and B in which A is a polymerized derivative of a perfluorinated cyclic or cyclizable organic compound, and B has the formula

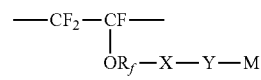

in which X is $SO_2$ or CO, Y is $NSO_2R_f^1$ or O, $R_f$ and $R_f^1$ are each independently perfluoroalkyl or perfluoroalkylether groups having 1-20 carbon atoms, and M is a Group 11 metal, and in which the metal exchanged fluorinated ionomer is dissolved in the liquid solvent system.

DETAILED DESCRIPTION OF THE INVENTION

This invention is directed to separating olefins from mixtures (occasionally herein, "feed mixtures") of olefins with paraffins. "Olefins" refers to chemical compounds having at least one carbon-carbon double bond. Other functional groups, such as ketone, esters, or alcohols may also be present. Paraffins refers to chemical compounds free from carbon-carbon double bonds. Preferred olefins in this invention are mono-saturated hydrocarbons of the formula $C_nH_{2n}$ wherein n is 2 to 30. Preferred paraffins are saturated hydrocarbons of the formula $C_nH_{2n+2}$ wherein n is 2 to 30 The invention is very effective for separating an olefin having a particular number of carbon atoms in the range of 2-30 from a feed mixture comprising that olefin and the paraffin that has the same number of carbon atoms. The feed mixture can include more olefins and paraffins than the one olefin and one paraffin that have the common particular number of carbon atoms. Often the feed mixture is in the gaseous state.

A glossary of abbreviations used in this disclosure is presented in Table I.

TABLE I

Glossary

| | |
|---|---|
| IEPP | Group 11 metal ion-exchanged PDD/SEFVE copolymer, e.g., PDD/SEFVE-M |
| PDD | perfluoro-2,2-dimethyl-1,3-dioxole |
| SEFVE | $CF_2$=$CFOCF_2CF(CF_3)OCF_2CF_2SO_2F$ |
| SEFVE-H | $CF_2$=$CFOCF_2CF(CF_3)OCF_2CF_2SO_3H$ |
| POESF | perfluoro(3-oxapent-4-ene)sulfonyl fluoride $CF_2$=$CFOCF_2CF_2SO_2F$ |

In various aspects this invention relates to novel methods of making and using a new metal ion exchange polymer, more specifically, a metal exchanged fluorinated ionomer. This ionomer comprises at least two types of repeating units "A" and "B" in random order with a generalized $-[A]_m-[B]_n$ backbone configuration. A is a polymerized derivative of a perfluorinated cyclic or cyclizable organic compound. B is a highly polymerized derivative of a fluorinated vinylether compound in which the acid moiety is exchanged with a cation of Group 11 metals. With greater specificity, the metal exchanged fluorinated ionomer thus has a structure of formula (1)

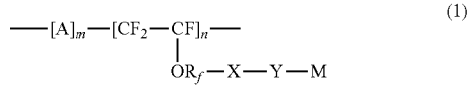

(1)

in which

A is the polymerized derivative of perfluorinated cyclic or cyclizable organic compound, m and n are the respective fractions of total number of repeating units A and the highly fluorinated vinylether compound derivative in the ionomer, X is $SO_2$ or CO, Y is $NSO_2Rf^1$ or O, $R_f$ and $R_f^1$ are each independently perfluoroalkyl or perfluoroalkylether groups having 1-20 carbon atoms, and M is a Group 11 metal.

The metal exchanged fluorinated ionomer can be formed by several copolymerization strategies. These involve copolymerizing appropriate perfluorinated cyclic or cyclizable organic compound monomers and highly fluorinated vinylether compound monomers selected to obtain desired repeating units A and B, respectively. Preferably the vinylether compound is perfluorinated. When X=$SO_2$, it is preferred to polymerize the vinylether compound having structure as in formula (1) in which the Y moiety is F, as illustrated by the monomer SEFVE. The sulfonyl fluoride group in the resulting copolymer can be hydrolyzed and acidified to the acid form in which OH replaces F. The acidic hydrogen is then exchanged with a metal salt of M to obtain the metal exchanged fluorinated ionomer. In an alternate embodiment, the sulfonyl fluoride group of the resulting copolymer with X=$SO_2$ can be reacted with a sulfonamide of structure $HNSO_2R_f^1$ to form copolymeric sulfonimide compound having structure as in formula (1) in which moiety Y is $NSO_2R_f^1$ and moiety designated "M" is H. The acidic hydrogen on nitrogen is then exchanged with a metal salt of M to obtain the metal exchanged fluorinated ionomer. When X=CO, it is preferred to polymerize the monomer of the vinylether compound in which moiety designated "Y" is methoxy group $OCH_3$. The resulting polymer can be hydrolyzed and acidified to form the acid polymer with X=CO, Y=O and moiety designated "M"=H. The acidic hydrogen is then exchanged with a metal salt of M to obtain the metal exchanged fluorinated ionomer.

Another strategy calls for copolymerizing the perfluorinated cyclic or cyclizable organic compound monomer with the monomer that is the acid form of the highly fluorinated vinylether compound and then exchanging the terminal hydrogen atom of the $R_f$ or $R_f^1$ group with M. It is also contemplated that the perfluorinated cyclic or cyclizable organic compound monomer can be copolymerized with comonomer being the metal ion exchanged form of the highly fluorinated vinylether compound to directly yield the metal exchanged fluorinated ionomer.

Preferred Group 11 metals, M, are silver and copper.

Representative examples of the perfluorinated cyclic or cyclizable organic compound are perfluoro-2,2-dimethyl-1, 3-dioxole ("PDD"). perfluoro-2-methylene-4-methyl-1,3-dioxolane ("PMD"), perfluoro (alkenyl vinylether) ("PFVE"), and 2,2,4-trifluoro-5 trifluoromethoxy-1,3 dioxole ("TFMD"). PDD is preferred.

Representative examples of the highly fluorinated vinylether compound are vinylethers containing sulfonyl fluoride such as SEFVE, CF2=CFOCF2CF2SO2F and CF2=CFOCF2CF2CF2CF2SO2F, and vinylether carboxylates such as CF2=CFOCF2CF(CF3)OCF2CF2CO2CH3. The preferred highly fluorinated vinylether compound is SEFVE.

The ionomer can optionally include additional repeating units of polymerized fluorinated compounds, with the proviso that repeating units A and B are also present. Representative of such additional repeating units are those of formula (1) disclosed by Watakabe et al. in U.S. Pat. No. 7,220,508, the disclosure of which is hereby incorporated by reference herein, and the polymerized monomers chlorotrifluoroethylene (CTFE), vinylidene fluoride (VDF), trifluoroethylene (TrFE). and blends thereof. A preferred metal exchanged fluorinated ionomer according to this invention is poly(PDD/SEFVE) sometimes preferred to as "IEPP" ionomer. It is a copolymer of PDD and SEFVE in which the fluorine atom of the terminal sulfonylfluoride group is replaced by an oxygen and a metal ion. The structure of IEPP ionomer is shown in formula (2) below in which 0<m<1.0 and n=1.0−m, and M=Ag.

According to this invention silver metal ion exchanged ionomers of formula (2) have been discovered to provide excellent permeability and selectivity when used as the active layer of a selectively gas permeable membrane for the separation of olefins from mixtures with paraffins. Without wishing to be bound by a particular theory, it is believed that the silver facilitates the transport of the olefin. Other metal ions that may be used include copper and gold.

The proportions of repeating units A to repeating units B in the polymer chain, i.e., m:n ratio, for highly effective selectively permeable ionomers can range widely. Preferably the mole fraction of repeat units B in the ionomer is at least about 0.05, preferably at least about 0.1, more preferably at least about 0.2, and most preferably at least about 0.4. The preferable mole fraction of repeat units B is at most about 0.5 The mole fraction of repeat units A is at least about 0.3 and, when no optionally additional fluorinated compound repeating units are present, will be an amount complementary to B totaling to 1.0.

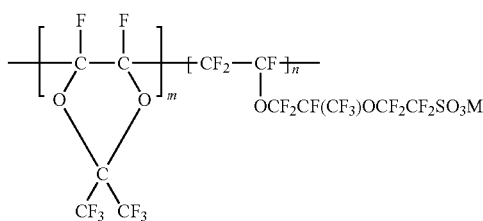

(2)

One embodiment of a method of making the novel ionomer involves multiple steps generally beginning with copolymerizing A and B precursor monomers and then hydrolyzing the resulting polymer to replace terminal sulfonyl fluoride atoms with hydrogen to produce an acid form ionomer. For example in which IEPP ionomer is synthesized from PDD and SEFVE comonomers, the acid form precursor ionomer poly(PPD/SEFVE-H) has structure as shown in formula (3). Watakabe et al. U.S. Pat. No. 7,220,508 discloses a procedure suitable for making this poly(PPD/SEFVE-H) precursor that is exemplified in U.S. Pat. No. '508 Examples 1 and 2. The disclosure of U.S. Pat. No. '508 along with entire disclosures of all U.S. patents and patent applications identified in this application are hereby incorporated by reference herein.

Eriksen et al., U.S. Pat. No. 5,191,151, discloses copolymerization of tetrafluoroethylene ("TFE") and SEFVE and methods of exchanging the sulfonic acid hydrogen ion with a Ag cation. Eriksen's methods involve many steps that include contacting the TFE/SEFVE-H ionomer with an alkali metal solution to exchange the alkali metal in the ionomer, exposing the alkali exchanged ionomer to an alcohol to swell the ionomer, and then contacting the swollen alkali metal exchanged fluorinated ionomer with a silver-containing aqueous solution to obtain a silver exchanged ionomer. Additional preferred steps include separating the alkali metal exchanged fluorinated ionomer from excess alkali metal solution and heating the alkali metal exchanged fluorinated ionomer to about 100-350° C. for up to 3 hours prior to swelling, removing excess alcohol from the swollen alkali metal exchanged fluorinated ionomer, and removing excess silver solution from the silver exchanged ionomer. Eriksen discloses that the silver exchanged TFE/SEFVE ionomer is useful for separating $C_2$-$C_4$ olefins from $C_1$-$C_6$ paraffins.

The present novel method provides a simpler and very efficient way to obtain an operative metal exchanged fluorinated ionomer for use in membranes having superior ability to separate olefins from mixtures with paraffins. This method starts by dissolving precursor poly(PDD/SEFVE-H) ionomer (formula (3)) in an appropriate solvent.

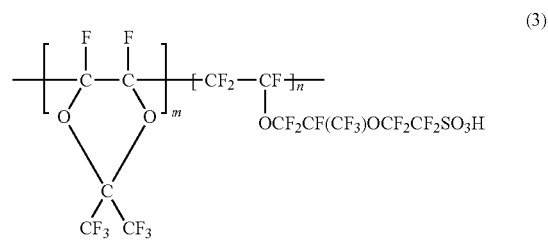

(3)

An advantageous feature of the novel metal exchanged fluorinated ionomers, such as PDD/SEFVE ("IEPP") ionomers and corresponding precursor acid form ionomers, is that they are soluble in liquid mixtures of fluorosolvents and common, non-fluorinated, polar solvents. Some of the novel metal exchanged fluorinated ionomers are soluble in liquid that consists essentially of polar solvents. In this context, the term "consists essentially of polar solvents" means that the solvent system exclusively utilizes polar solvents or optional other components, but is substantially free of very fluorinated solvents known and selected for ability to dissolve highly and perfluorinated polymers. The optional other components are usually in minor proportions, and do not materially affect the basic and novel characteristics of the invention.

The relative fractions of PDD and SEFVE monomers in the copolymer determine whether a fluorosolvent is called for. Generally, metal exchanged fluorinated ionomer containing up to about 20 mole % polymerized SEFVE will be soluble in mixtures of fluorinated solvent and common polar solvent. IEPP containing more than about 20 mole % SEFVE can dissolve in polar solvents alone. Accordingly; for many compositions, use of extraordinary and usually high priced fluorinated solvents is avoided. Products such as thin film membranes of IEPP metal exchanged fluorinated ionomer can be made at reasonable cost using easily obtainable solvents by industry standard liquid deposition techniques such as dipping, spraying, roller coating, doctoring and the like.

Representative common polar solvents that are suitable to solubilize IEPP copolymers include methanol, ethanol, isopropanol, ethyl chloride, methyl chloride and methylene chloride, dimethylformamide, dimethylsulfoxide, sulfolane, N,N'-dimethyl-imidazolidinone, benzyl alcohol, phenol, cresol and the like.

Representative fluorosolvents that are primarily intended for solubilizing fluorinated polymers and that are suitable for use in the novel process include perfluoroalkanes, such as perfluorohexane, perfluoroheptane and perfluorooctane, available from 3M Company, Minneapolis, Minn. under the tradenames PF5060, PF5070 and PF5080, respectively. Other representative fluorinated solvent materials that can be used include Fluorinert™ FC-75 and FC-770 Electronic Liquids, and Novec™ HFE-7100, Novec™ HFE-7200, and Novec™ 7300 Engineered Fluids also from 3M. Fluorinert FC-75 is a solvent of perfluorinated compounds primarily with 8 carbons, believed to include 2-butyltetrahydrofuran. Fluorinert FC770 contains C1-C3 perfluoro N-alkyl morpholines among other perfluorinated compounds. Novec HFE-7100 includes methyl nonafluoroisobutyl ether and methyl nonafluorobutyl ether. Novec HFE-7200 includes ethyl nonafluoroisobutyl ether and ethyl nonafluorobutyl ether. Novec 7300 contains 1,1,1,2,2,3,4,5,5,5-decafluoro-3-methoxy-4-(trifluoromethyl)-pentane.

Further in the method of making the ionomer according to this invention, the acid form precursor PDD/SEFVE-H ionomer can be dissolved in merely ordinary polar organic solvent, such as ethyl alcohol, provided that the mole fraction of SEFVE repeating units of the polymer is at least about 0.2. If the SEFVE repeating unit mole fraction is less, then either a specialty, fluorinated solvent or a blend of polar organic and fluorinated solvents can be used.

A subsequent step of the novel method calls for charging a solid metal salt directly to the ionomer solution. The metal salt should be in fine particulate form and poorly soluble in the in the ionomer solution. By "poorly soluble" is meant that the metal salt solubility should be at most about 10 g/L, preferably at most about 5 g/L, more preferably at most about 2 g/L and most preferably at most about 1 g/L. Great preference is given for the metal salt to be insoluble in the ionomer solution, that is, at most about 0.01 g/l. The preferred metal suitable for the ion used with this is silver. Silver salt of any composition that satisfies the particle size and solubility criteria just mentioned may be used. Representative silver salt compounds include silver carbonate, cyanide, diethyldithiocarbamate, iodate, nitrate, oxide, phosphate, sulfate, acetate, bromide. The solid silver may be heated prior to adding to adding to the solution to facilitate exchange reaction with the polymer. However, the salt temperature should not be raised to a point that adversely affects the polymer. With metal salt added solution should be heated to reflux temperature of the solution solvent to disassociate the metal ion from the salt. By way of example, when silver carbonate is the salt, reflux will release carbon dioxide and silver will associate with the polymer by ion exchange. Typically the temperature is in the range of about 30-100° C. The ionomer/solvent solution should be agitated effectively to maintain the silver salt in suspension. Typically ion exchange occurs within about an hour. Thereafter the solution can be cooled to room temperature. The excess solid silver salt is then filtered from the ionomer solution. Finally, the polymer can be isolated from the filtrate solution by evaporating the solvent using heat and vacuum.

In another aspect, the ionomer can be converted from acid to metal form by contacting a solution of a soluble metal salt in an appropriate solvent that is a non-solvent for the ionomer being converted. Thus following exchange, the metal bearing ionomer precipitates. Then the dispersion is heated, cooled, and filtered and rinsed to isolate metal exchanged fluorinated ionomer from the solution. By way of example, solid ionomer can be dispersed in a salt solution of aqueous silver nitrate. The dispersion is heated, typically for up to several hours, cooled, filtered and the solids rinsed with water to yield silver-exchanged ionomer.

Both conversion methods described above involve heterogeneity of the polymer and metal salt component phases. In the former, the polymer in solution contacts a solid form metal salt. In the latter, the solid polymer is contacted by soluble salt in solution. A main advantageous feature of these methods is that the metal is exchange into the ionomer is substantially complete without an excess of free metal salt present in the polymer product.

In another embodiment for making the novel polymer, the second monomer, e.g., SEFVE is initially hydrolyzed to acid form SEFVE-H. The hydrolyzed intermediate is then converted to the desired metal salt. The second monomer in metal salt form can then be polymerized with the acyclic or cyclizable fluorinated first monomer, e.g., PDD. A polar fluorinated solvent, such as trifluoroacetic acid can be used to provide a suitably soluble reaction medium for the first monomer. The resulting polymer can be isolated from the polymerization mass and used to form a membrane without further purification.

According to the above-described method metal of insoluble metal salt can be exchanged with polymer in solution. This provides a further distinct advantage that the novel ion exchanged ionomer can be cast from solution to form a thin film nonporous selectively permeable gas separation membrane. Thus for example, after filtering excess silver carbonate, the IEPP ionomer solution can be formed into a membrane without an intermediate step of isolating the IEPP ionomer in solid form. All types of conventional solvent casting membrane formation techniques can be used. Typically the solution is deposited as a thin film onto a porous support, excess fluid is drained and the wet IEPP ionomer solution solvent is evaporated to produce a composite membrane. Any type of membrane support suitable for solvent deposition can be used, such as flat sheet, pleated sheet, spiral wound, ribbon tube, hollow fiber and the like.

The novel membranes with non-porous active selectively permeable layers of IEPP are remarkably effective for separating olefins from mixtures with paraffins. They are especially useful for separating olefins and paraffins of similar molecular weight and size that are difficult to segregate by conventional methods. The extraordinary separation performance is shown in Table II.

Another significant feature of the novel membrane compositions and processes of this invention is that humidifying the olefin/paraffin feed gas mixture and/or the permeate olefin enriched product is not necessary to achieve commercially productive separation performance. This is a departure from traditional membrane separation of olefin/paraffin mixtures typified by processes disclosed in Eriksen U.S. Pat. No. 5,191,151 that call for the presence of water vapor in the gaseous streams of silver-exchanged ionomer membranes. Optionally according to this invention the feed and/or permeate gas mixtures may be humidified. With humidification this invention has been discovered to provide far superior separation performance of olefins from paraffins than is obtained by comparable conventional membrane processes.

EXAMPLES

This invention is now illustrated by examples of certain representative embodiments thereof, wherein all parts, proportions and percentages are by weight unless otherwise indicated. All units of weight and measure not originally obtained in SI units have been converted to SI units. Unless otherwise indicated, pressure values recited throughout this disclosure are gage pressures, i.e., relative to atmospheric pressure.

Example 1: Forming Silver-Exchanged PDD-SEFVE Copolymer

Into a glass pressure tube were placed 4.88 g PDD, 17.84 g SEFVE, 5 mL 2,3-dihydrodecafluoropentane (Vertrel® XF specialty fluid, DuPont Wilmington, Del.), and 1 mL initiator solution in Vertrel® XF of hexafluoropropylene oxide (HFPO) dimer peroxide made from reaction of $CF_3CF_2CF_2OCF(CF_3)CFO$ with basic hydrogen peroxide. The tube was cooled to −78° C. in a dry ice/isopropanol bath, evacuated and filled with nitrogen 3 times. The glass tube was sealed, allowed to warm to room temperature in a water bath. The reaction mixture was agitated by shaking overnight. The tube was opened to ambient air and 20 mL acetone was added into the mixture. After stirring for 15 minutes, the liquid was decanted and 20 mL fresh acetone was added. After stirring for 15 minutes, the liquid was again decanted and the solid residue was transferred to a watch glass. Drying in an oven at 100° C. overnight yielded 6.3 g of white, solid PDD/SEFVE copolymer product.

The PDD/SEFVE copolymer was hydrolyzed with KOH dissolved in a water/ethanol mixed solvent solution, filtered from solution, and then immersed in an aqueous nitric acid solution, drained and re-immersed to convert to the acid form of the polymer. The acid form polymer was then filtered and rinsed with deionized water and dried under vacuum to obtain poly(PDD/SEFVE-H) copolymer.

Poly(PDD/SEFVE-H) copolymer (4.9 g) was dissolved in 50 ml of ethyl alcohol at room temperature, i.e., about 25° C. While stirring the solution 1.0 g Ag2CO3 powder was added to obtain a suspension. The suspension was heated close to the boiling point of ethyl alcohol and refluxed for 1 hour. The suspension was then cooled to room temperature and then filtered to remove residual solid Ag2CO3 from the solution. The filtrate solvent was evaporated by oven drying at 100° C. for 1 hour to yield 4.0 g dry yellow granules of IEPP(Ag+) silver exchanged copolymer.

The copolymer thus produced is acceptable for practical uses. However, this process can entrain reduced silver not bound to the polymer chain. To recover that reduced silver metal back to polymeric ionic silver, the following optional additional steps can be performed. The yellow granules can be repetitively rinsed with dilute hydrogen peroxide and water and re-filtered to obtain a white powder of copolymer.

Example 2: Making a Membrane of Silver-Exchanged PDD-SEFVE Polymer

An IEPP(Ag$^+$) copolymer having about 60 mole % PDD repeating units and about 40 mole % SEFVE repeating units was made by a procedure as in Ex. 1. The copolymer was dissolved at room temperature in a solution of 70 wt % isopropyl alcohol and 30 wt % Novec 7300 fluid to make 1.2 wt % polymer solution. An asymmetrically porous sheet of polyacrylonitrile (PAN) microfiltration membrane was dipped into the polymer solution. The wet sheet was removed and held vertically to drain the excess liquid. The copolymer-coated membrane was then dried in an oven at 100° C. overnight to form a non-porous composite membrane.

Examples 3-5 Separation of Propane and Propylene Using IEPP(Ag$^+$) Membranes

Several PAN substrate membranes coated with IEPP (Ag$^+$) having different ratios of PDD:SEFVE were made by a procedure substantially as described in Ex. 2. Each membrane was placed in a permeation test cell. A dry gas mixture of 80 wt % propane and 20 wt % propylene was fed at 69 kPa (10 psi) to one side of the cell at a flow rate of 200 standard cm$^3$ ("scc") per min. maintained by mass flow controllers. The gas mixture permeated the nonporous membranes and permeate stream flow was measured by a bubble flow meter. Nitrogen gas was swept across the permeate side of the membrane at rates in the range of 25-200 scc/min. Concentrations of the propane and propylene in the permeate were determined by Fourier transform infrared spectroscopic analysis using a Nicolet® 6700 FTIR analyzer (Thermo Fisher Scientific, Waltham Mass.) equipped with a 2 m gas cell path length. Flow rates were adjusted such that stage cut (i.e., flow of permeate relative to flow of feed) was maintained below 10%. Permeance was calculated for each component independently using the log mean partial pressure difference across the membrane. Selectivity was calculated as the ratio of propylene permeance to propane permeance. Resulting data is presented in Table II.

Examples 6 and 7

The procedures of Ex. 4 and 5 were repeated except that the feed and sweep streams were bubbled through water at room temperature at flow rates in the range of 25-200 scc/min. The humidified streams produced increased permeance as seen by results presented in Table II.

TABLE II

| | SEFVE in IEPP(Ag$^+$) (mole %) | Propane Permeance (GPU) | Propylene Permeance (GPU) | Propylene to Propane Selectivity |
|---|---|---|---|---|
| Ex. 3 | 20 | 0.5 | 11 | 22 |
| Ex. 4 | 30 | 0.2 | 6.8 | 34 |
| Ex. 5 | 40 | 0.2 | 16 | 80 |
| Ex. 6 | 30 | | 307 | 41 |
| Ex. 7 | 40 | | 215 | 72 |

Example 8: Forming Silver-Exchanged Sulfonimide Copolymer

A copolymer was synthesised from a 100:200 PDD: SEFVE mole ratio comonomer feed mixture. Into a glass beaker was placed 2 g of the PDD/SEFVE copolymer, 0.43 g of trifluoromethylsulfonamide $CF_3SO_2NH_2$, 100 mL Novec HFE 7200 fluorinated solvent, 50 mL tetrahydrofuran and 0.72 g of triethylamine. The mixture was stirred at 70° C. for 24 hours. Thereafter solvents were evaporated leaving a granular product. A copious quantity of water was added to the product that was then filtered. The solid product was immersed in 10 mL of 3N aqueous hydrochloric acid and stirred for 3 hours. After filtering, the product was again water washed, filtered, and dried under vacuum to yield 1.8 g PDD/SEFVE-imide copolymer with repeating unit A of polymerized PDD and repeating unit B of $CF_2$—CF $(OCF_2CF(CF_3)OCF_2CF_2SO_2NHSO_2CF_3)$.

The PDD/SEFVE-imide (0.5 g) was mixed in 10 mL water with 85 mg of silver carbonate powder and stirred about 12 hours to exchange silver ions for protons. The solid product was filtered and washed with water after which 10 mL of 10 wt % hydrogen peroxide was added. The mixture was stirred for 24 hours, then filtered and the solid silver-exchanged PDD/SEFVE-imide ionomer was washed with water, and dried under vacuum. A coating solution of 2 wt % of the silver-exchanged PDD/SEFVE-imide ionomer dissolved in 30 wt % Novec HFE 7300/70 wt % isopropyl alcohol mixture was prepared. The solution was coated by the procedure as in Ex. 2 onto a PAN microporous substrate to form a membrane. The membrane was tested (Ex. 8a) by permeating a 20 wt % propylene/80 wt % propane gas mixture at 60 psi (414 kPa) using the procedure described in Exs. 3-5. Selectivity was calculated from measurements of component permeances. The permeation procedure was repeated (Ex. 8b). Results are shown in Table III.

Example 9: Ethylene and Ethane Pure Gases Permeated Through PDD-SEFVE-Ag+ Membrane Fabricated with Mixed Solvent Solution A PDD/SEFVE-silver exchanged ionomer was prepared as in Ex. 1. A 2 wt % solution of this ionomer in a 30 wt % Novec HFE 7300/70 wt % isopropyl alcohol solvent mixture was coated on a PAN substrate to fabricate a membrane as described in Ex. 2. The membrane was evaluated by permeating pure ethylene and ethane gases separately in duplicate trials (9a, 9b) at the same pressure. A second membrane of same composition was also prepared and the same evaluation was repeated at lower pressure (9c). Results are presented in Table III.

Example 10: Ethylene/Ethane Permeation Through PDD-SEFVE-VF$_2$—Ag+ Membrane Fabricated with Mixed Solvent Solution The procedure of Example 9 was repeated except that the copolymer that was silver exchanged had composition produced from a 21.4 mole % PDD/57.2 mole % SEFVE/21.4 mole % vinylidene fluoride (VF2), i.e., 100:267:100 mole ratio, feed mixture. The membrane was tested by separately permeating pure ethylene and ethane gases at three different membrane feed pressures. Results are presented in Table III.

Example 11: Propylene/Propane Separations with PDD-POESF-Ag+ Membrane

The copolymer synthesis procedure of Ex. 1 was repeated except that the highly fluorinated vinylether compound monomer was perfluoro(3-oxapent-4-ene)sulfonyl fluoride "POESF" (SynQuest Laboratories Inc. Alachua, Fla.), to provide a silver exchanged ionomer based on 100:200 PDD:POESF reactant mole ratio. A membrane of this ionomer was fabricated by a procedure similar to Ex. 2. The membrane was mounted into a permeation test cell. A gas mixture of 80 vol. % propane/20 vol. % propylene was humidified to 80% relative humidity ("RH") by bubbling through water at about 24° C. and then fed into the cell in contact with the feed side of the membrane. A similarly 80% RH humidified, nitrogen sweep gas stream of 300 mL/min at 2.8 kPa (0.4 psi) was blown through the cell on the permeate side. Duplicate trials (11a, 11b) were conducted and separation results are presented in Table III.

Example 12: Ethylene/Ethane Separations with PDD/SEFVE-Ag+ Membrane

A membrane of PDD/SEFVE copolymer with silver counter ion was fabricated as in Ex. 2. A 10 vol. % ethylene/90 vol. % ethane gas mixture was separated by the membrane in duplicate trials. Results are shown in Table III.

Example 13: Propylene/Propane Membrane Separations with PDD-SEFVE-VF$_2$-Ag+ Membrane Fabricated with Mixed Solvent Solution A membrane of PDD-SEFVE-VF$_2$—Ag+ copolymer was prepared as in Ex. 10. The membrane was used in several trials of separating propylene/propane gas mixtures. In each of these trials, a humidified nitrogen sweep gas stream of 300 mL/min was blown through the permeate side of the membrane at 2.8 kPa (0.4 psi). Humidity of the sweep for trials 13a-13c were respectively 87%, 77%, and 81% RH, respectively. Feed gas mixtures were 10° C., 15° C., and 23° C., and were humidified to 85%, 84% and 81% RH, in trials 13a-13c, respectively. Data is presented in Table III.

Example 14: Olefin/Paraffin Facilitated Transport Membrane Separation with Condensable Sweep Gas A membrane was fabricated as in Example 2, and used in successive trials of separating a 414 kPa (60 psi) pressurized, 10 vol. % propylene/90 vol. % propane, room temperature gas mixture. Various sweep gas configurations were employed in the trials. In trial 14a, the feed mixture was not humidified. The vapor above a sealed tank of water was admitted via a transfer line to the permeate chamber of the test cell and drawn across the permeate side of the membrane under vacuum of 6.7 kPa (50 Torr) absolute pressure as a sweep gas. Trial 14b was the same except that the transfer line closed such that the permeate side was maintained under dry vacuum and the feed was not humidified. For trial 14c, a humidified nitrogen gas sweep blown through the permeate side of the membrane cell at 2.8 kPa (0.4 psi) was used and the feed mixture was also humidified. Data are presented in Table III.

Ex. 14c demonstrates that excellent olefin-to-paraffin selectivity and olefin permeance is obtained with a facilitated transport membrane according to this invention. Due to the inert gas from the sweep stream, the permeate stream usually would need further separation in additional unit operations to remove the inert gas and become suitable for practical use as a chemical process raw material. By comparison, Ex. 14a provides equivalent high olefin-to-paraffin selectivity and moderately lower yet remarkably high olefin permeance. However, this configuration presents the likely more significantly advantageous feature that the sweep stream contains no non-condensable vapor component, such as nitrogen or other inert gas. Consequently, no non-condensable vapor component other than olefin and paraffin is present in the permeate. By "non-condensable" is meant that the vapor component does not substantially completely condense from the gas state at upon exposure to temperature in the range of about −40° C. to about 0° C. and absolute pressure in the range of about 1.3 kPa (10 mmHg) to about 101 kPa (760 mmHg). Consequently highly enriched olefin product can be relatively simply obtained by merely processing the humid permeate stream through a low temperature condenser to condense and drain entrained water vapor. An additional separation of non-hydrocarbon inert sweep compound from the olefin enriched permeate is thus avoided.

The effect of water vapor in the sweep of Ex. 14a is seen by comparison with Ex. 14b. With a dry vacuum sweep the permeance is reduced by about 50%. However, olefin-to-paraffin selectivity is about the same as in Exs. 14a. Thus the novel membrane continues to be excellent for discriminating between olefin and paraffin. Without wishing to be bound by a particular theory, the high olefin transfer rate with water vapor sweep is thought to be due to water-motivated, enhanced facilitated transfer activity within the membrane. Higher olefin permeance has been known to occur in facilitated transfer membranes in which the feed is humidified, such as in Ex. 14c. That was understood to result from water molecules being drawn into the membrane with the permeating feed. Comparison of 14a and 14b suggests that unexpected moisture vapor contact only on the permeate side of the membrane is able to engender some enhanced facilitated transfer activity within the membrane such that significantly higher olefin permeance is achieved.

Another advantage of humidifying only sweep on the permeate side is that the feed stream need not be humidified and, consequently, the retentate stream contains only a small amount of water vapor. The water vapor transferring through the membrane from the humidified permeate sweep stream to enter the retentate will thus be less than occurs when using a humidified feed stream.

Although specific forms of the invention have been selected in the preceding disclosure for illustration in specific terms for the purpose of describing these forms of the invention fully and amply for one of average skill in the pertinent art, it should be understood that various substitutions and modifications which bring about substantially equivalent or superior results and/or performance are deemed to be within the scope of the following claims.

TABLE III

| | Membrane A repeat unit | Membrane A feed mole % | Membrane B repeat unit | Membrane B feed mole % | Membrane Other repeat unit | Membrane Other feed mole % | Olefin "O" | Paraffin "P" | Feed type O/P vol/vol | Feed Gas Pressure psi (kPa) | Olefin Permeance (GPU) | Paraffin Permeance (GPU) | Olefin to Paraffin Selectivity |
|---|---|---|---|---|---|---|---|---|---|---|---|---|---|
| Ex. 8a | PDD | 33.3 | SEFVE-imide | 66.7 | | | $C_3H_6$ | $C_3H_8$ | 20/80 mix | 60 (414) | 182.7 | 11.9 | 12.6 |
| Ex. 8b | PDD | 33.3 | SEFVE-imide | 66.7 | | | $C_3H_6$ | $C_3H_8$ | 20/80 mix | 60 (414) | 113.0 | 7.8 | 13.9 |
| Ex. 9a | PDD | 33.3 | SEFVE | 66.7 | | | $C_2H_4$ | $C_2H_6$ | pure gases | 60 (414) | 204.6 | 24.3 | 8.4 |
| Ex. 9b | PDD | 33.3 | SEFVE | 66.7 | | | $C_2H_4$ | $C_2H_6$ | pure gases | 60 (414) | 134.4 | 9.7 | 13.9 |
| Ex. 9c | PDD | 33.3 | SEFVE | 66.7 | | | $C_2H_4$ | $C_2H_6$ | pure gases | 30 (207) | 245.3 | 15.7 | 15.6 |
| Ex. 10a | PDD | 21.4 | SEFVE | 57.2 | $VF_2$ | 21.4 | $C_2H_4$ | $C_2H_6$ | pure gases | 30 (207) | 388.4 | 21.0 | 18.5 |
| Ex. 10b | PDD | 21.4 | SEFVE | 57.2 | $VF_2$ | 21.4 | $C_2H_4$ | $C_2H_6$ | pure gases | 45 (310) | 303.4 | 25.9 | 11.7 |
| Ex. 10c | PDD | 21.4 | SEFVE | 57.2 | $VF_2$ | 21.4 | $C_2H_4$ | $C_2H_6$ | pure gases | 60 (414) | 238.9 | 26.5 | 9.0 |
| Ex. 11a | PDD | 33.3 | POESF | 66.7 | | | $C_3H_6$ | $C_3H_8$ | 20/80 mix | 60 (414) | 298.3 | 11.9 | 25.2 |
| Ex. 11b | PDD | 33.3 | POESF | 66.7 | | | $C_3H_6$ | $C_3H_8$ | 20/80 mix | 60 (414) | 224.4 | 7.8 | 28.8 |
| Ex. 12a | PDD | 33.3 | SEFVE | 66.7 | | | $C_2H_4$ | $C_2H_6$ | 10/90 mix | 45 (310) | 294.6 | 1.9 | 156.8 |
| Ex. 12b | PDD | 33.3 | SEFVE | 66.7 | | | $C_2H_4$ | $C_2H_6$ | 10/90 mix | 45 (310) | 251.3 | 2.3 | 110.7 |
| Ex. 13a | PDD | 21.4 | SEFVE | 57.2 | $VF_2$ | 21.4 | $C_3H_6$ | $C_3H_8$ | 20/80 mix | 60 (414) | 35.3 | 2.6 | 13.8 |
| Ex. 13b | PDD | 21.4 | SEFVE | 57.2 | $VF_2$ | 21.4 | $C_3H_6$ | $C_3H_8$ | 20/80 mix | 60 (414) | 48.0 | 2.5 | 19.0 |
| Ex. 13c | PDD | 21.4 | SEFVE | 57.2 | $VF_2$ | 21.4 | $C_3H_6$ | $C_3H_8$ | 20/80 mix | 60 (414) | 101.4 | 3.4 | 30.0 |
| Ex. 14a | PDD | 33.3 | SEFVE | 66.7 | | | $C_3H_6$ | $C_3H_3$ | 10/90 mix | 60 (414) | 147.2 | 3.3 | 44.3 |
| Ex. 14b | PDD | 33.3 | SEFVE | 66.7 | | | $C_3H_6$ | $C_3H_8$ | 10/90 mix | 60 (414) | 60.3 | 1.3 | 45.1 |
| Ex. 14c | PDD | 33.3 | SEFVE | 66.7 | | | $C_3H_6$ | $C_3H_8$ | 10/90 mix | 60 (414) | 219.3 | 4.4 | 49.5 |

What is claimed is:

1. A neutral gas separation ionomer comprising repeat units A and B in which A is a polymerized derivative of a perfluorinated cyclic or cyclizable organic compound, and B has the formula

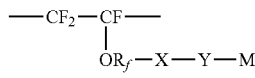

in which X is —$SO_2$— or —CO—, Y is —$O^-$ or —[$NSO_2R_f^1$]$^-$, $R_f$ is perfluoroalkylene optionally containing one or more ether groups, and having 1 to 20 carbon atoms, $R_f^1$ is perfluoroalkyl optionally containing one or more ether groups, and having 1 to 20 carbon atoms, and M is a Group 11 metal ion; wherein the neutral gas separation ionomer has a selectivity of propylene to propane of 9.0 or more.

2. The neutral gas separation ionomer as recited in claim 1 wherein the perfluorinated cyclic or cyclizable compound is selected from the group consisting of perfluoro-2,2-dimethyl-1,3-dioxole ("PDD"), perfluoro-2-methylene-4-methyl-1,3-dioxolane ("PMD"), perfluoro (alkenyl vinylether) ("PFVE"), and 2,2,4-trifluoro-5-trifluoromethoxy-1,3-dioxole ("TFMD").

3. The neutral gas separation ionomer as recited in claim 1 wherein $R_f$ is one or more of —$CF_2CF_2$—, —$CF_2CF(CF_3)OCF_2CF_2$—, or ($CF_2$)$_4$—.

4. The neutral gas separation ionomer as recited in claim 1 wherein M is silver.

5. The neutral gas separation ionomer as recited in claim 3 wherein M is silver.

6. The neutral gas separation ionomer as recited in claim 1, wherein repeat unit A has a concentration of at least 60 mole %.

7. A gas separation membrane comprising a nonporous selectively permeable membrane layer consisting essentially of a neutral gas separation ionomer as described in claim 1.

8. The gas separation membrane as recited in claim 7 wherein the perfluorinated cyclic or cyclizable compound is selected from the group consisting of perfluoro-2,2-dimethyl-1,3-dioxole ("PDD"), perfluoro-2-methylene-4-methyl-1,3-dioxolane ("PMD"), perfluoro (alkenyl vinylether) ("PFVE"), and 2,2,4-trifluoro-5-trifluoromethoxy-1,3-dioxole ("TFMD").

9. The gas separation membrane as recited in claim 8 wherein $R_f$ is one or more of —$CF_2CF_2$—, —$CF_2CF(CF_3)OCF_2CF_2$—, or —($CF_2$)$_4$—.

10. The gas separation membrane as recited in claim 7 wherein M is silver.

11. The gas separation membrane as recited in claim 9 wherein M is silver.

12. A method of separating one or more olefins from a mixture of said olefin with one or more paraffins, comprising, (A) providing one or more membranes comprising a nonporous layer of a neutral gas separation ionomer as described in claim 1;
(B) contacting a feed side of said membrane with said mixture; and
(C) applying a driving force to cause said olefins to preferentially permeate relative to said paraffins to a permeate side of said membrane.

13. The method of claim 12 wherein said feed mixture and permeate products are fluids, and in which the step of applying a driving force comprises contacting said permeate side of said membrane with a sweep fluid.

14. The method as recited in claim 13 in which said sweep fluid is a sweep gas which comprises an olefin, and a permeate product is at a lower pressure than the pressure of said mixture.

15. The method of claim 14 wherein said feed mixture comprises a pair of compounds from the group consisting of (i) ethylene and ethane, (ii) propylene and propane, or (iii) a butene and butane.

16. A solution of a neutral gas separation ionomer as described in claim 1 in a polar solvent system.

17. The solution of neutral gas separation ionomer as recited in claim 16 wherein said polar solvent system comprises about 10-100 vol. % organic polar solvent and a complementary amount of fluorinated solvent to total 100 vol %.

18. The solution of neutral gas separation ionomer as recited in claim 17 wherein said polar solvent system consists essentially of organic polar solvent.

19. The solution of neutral gas separation ionomer as recited in claim 16 wherein said perfluorinated cyclic or cyclizable compound is selected from the group consisting of perfluoro-2,2-dimethyl-1,3-dioxole, perfluoro-2-methylene-4-methyl-1,3-dioxolane), a perfluoro(alkenyl vinyl ether), or 2,2,4-trifluoro-5-trifluoromethoxy-1,3-dioxole.

\* \* \* \* \*